US012220469B2

(12) United States Patent
Nguyen et al.

(10) Patent No.: US 12,220,469 B2
(45) Date of Patent: Feb. 11, 2025

(54) SOLID W/O COSMETIC COMPOSITION

(71) Applicant: SHISEIDO COMPANY, LTD., Tokyo (JP)

(72) Inventors: Lethu Nguyen, East Windsor, NJ (US); Shoji Tajima, Yokohama (JP); Michelle Lou, East Windsor, NJ (US)

(73) Assignee: SHISEIDO COMPANY, LTD., Tokyo (JP)

(*) Notice: Subject to any disclaimer, the term of this patent is extended or adjusted under 35 U.S.C. 154(b) by 320 days.

(21) Appl. No.: 16/648,289

(22) PCT Filed: Feb. 6, 2019

(86) PCT No.: PCT/JP2019/004255
§ 371 (c)(1),
(2) Date: Mar. 18, 2020

(87) PCT Pub. No.: WO2019/156123
PCT Pub. Date: Aug. 15, 2019

(65) Prior Publication Data
US 2020/0214948 A1 Jul. 9, 2020

Related U.S. Application Data

(60) Provisional application No. 62/627,454, filed on Feb. 7, 2018.

(51) Int. Cl.
A61K 8/06 (2006.01)
A61K 8/73 (2006.01)
A61K 8/81 (2006.01)
A61Q 1/06 (2006.01)

(52) U.S. Cl.
CPC ............ A61K 8/064 (2013.01); A61K 8/73 (2013.01); A61K 8/733 (2013.01); A61K 8/8117 (2013.01); A61Q 1/06 (2013.01)

(58) Field of Classification Search
None
See application file for complete search history.

(56) References Cited

U.S. PATENT DOCUMENTS

| 5,567,426 | A | | 10/1996 | Nadaud et al. | |
|---|---|---|---|---|---|
| 5,674,508 | A | * | 10/1997 | Deserable | A61K 8/04 424/401 |
| 5,756,082 | A | | 5/1998 | Cashin et al. | |
| 5,928,655 | A | | 7/1999 | Avalle | |
| 6,042,815 | A | * | 3/2000 | Kellner | A61Q 1/02 424/63 |
| 6,280,750 | B1 | | 8/2001 | Roulier et al. | |
| 6,528,073 | B2 | | 3/2003 | Roulier et al. | |
| 8,591,871 | B2 | * | 11/2013 | Do | A61Q 5/004 424/70.12 |
| 8,597,621 | B2 | | 12/2013 | Bui et al. | |
| 9,023,334 | B2 | | 5/2015 | Trabelsi | |
| 2003/0228339 | A1 | * | 12/2003 | El-Nokaly | A61K 8/044 424/401 |
| 2005/0118211 | A1 | * | 6/2005 | Nakamura | A61K 8/733 424/401 |
| 2005/0176871 | A1 | * | 8/2005 | Auguste | A61K 8/0208 524/505 |
| 2008/0226575 | A1 | * | 9/2008 | Hanna | A61K 8/8152 424/70.7 |
| 2010/0233220 | A1 | | 9/2010 | Ueda et al. | |
| 2011/0070177 | A1 | * | 3/2011 | Arnaud | A61K 8/06 206/581 |
| 2012/0195841 | A1 | * | 8/2012 | Yoshida | A61K 8/4946 424/60 |
| 2012/0321578 | A1 | * | 12/2012 | Leuridan | A61K 8/06 424/63 |
| 2017/0304658 | A1 | * | 10/2017 | Roudot | A61K 8/25 |
| 2019/0038526 | A1 | * | 2/2019 | Omura | A61K 8/064 |
| 2019/0388306 | A1 | * | 12/2019 | Ravni | A61K 8/0229 |

FOREIGN PATENT DOCUMENTS

| EP | 0 950 392 A1 | | 10/1999 | | |
|---|---|---|---|---|---|
| EP | 1 112 325 B1 | | 5/2003 | | |
| JP | H02-88513 A | | 3/1990 | | |
| JP | 2005-194248 A | | 7/2005 | | |
| JP | 2010-173997 A | | 8/2010 | | |
| JP | 2017-128512 A | | 7/2017 | | |
| KR | 100789345 B1 | * | 12/2007 | | |
| KR | 20130049053 A | * | 5/2013 | | |
| WO | WO-00/78868 A1 | | 12/2000 | | |
| WO | WO-2006028308 A1 | * | 3/2006 | | A61K 8/06 |
| WO | WO-2013092724 A1 | * | 6/2013 | | A45D 40/26 |
| WO | WO-2014/128679 A1 | | 8/2014 | | |

(Continued)

OTHER PUBLICATIONS

ShinEtsu Personal Care Silicones, 2021; https://www.shinetsusilicone-global.com/products/personalcare/products/polyether_modified_silicones.shtml (Year: 2021).*
Truth in Aging "Cetyl ethylhexanoate", printed 2021; https://www.truthinaging.com/ingredients/cetyl-ethylhexanoate (Year: 2021).*
Van Reeth et al. "New Formulating Options with Silicone Emulsifiers," 2004 (Year: 2004).*
Google search result for Van Reeth (Year: 2021).*
Google translation KR 10-0789345 B1, printed 2024 (Year: 2024).*
Google translation KR 2013-0049053 A, printed 2024 (Year: 2024).*
International Searching Authority, "International Search Report," issued in connection with International Patent Application No. PCT/JP2019/004255, dated May 7, 2019.
International Searching Authority, "Written Opinion," issued in connection with International Patent Application No. PCT/JP2019/004255, dated May 7, 2019.

(Continued)

Primary Examiner — David J Blanchard
Assistant Examiner — Alissa Prosser
(74) Attorney, Agent, or Firm — Foley & Lardner LLP

(57) ABSTRACT

A solid W/O stable composition comprising a gellifying system comprising at least one hydrophobic gelling agent and at least one hydrophilic gelling agent and an emulsifying system comprising at least one surfactant having HLB value of 14 or less. Further there is disclosed a method of treatment keratinous surface with the inventive composition.

11 Claims, No Drawings

(56) References Cited

FOREIGN PATENT DOCUMENTS

| WO | WO-2016017188 A2 | * | 2/2016 | ............... A61K 8/31 |
| WO | WO-2016157957 A1 | * | 10/2016 | ........... A61K 8/0208 |
| WO | WO-2017126252 A1 | * | 7/2017 | ............ A61K 8/064 |
| WO | WO-2018142076 A1 | * | 8/2018 | ........... A61K 8/0229 |

OTHER PUBLICATIONS

European Extended Search Report from EP 19751180.1 dated Jun. 1, 2021(9 pages).
Mintel Information "VisionAiry Gel Lipstick" (2018) http://www.gnpd.com (7 pages).
Office Action issued in corresponding Japanese Patent Application No. 2020-540655, dated Dec. 20, 2022.
Office Action cited in corresponding Chinese Patent Application No. 201980005272.1, dated Sep. 5, 2022.
Office Action issued in corresponding Chinese Patent Application No. 201980005272.1, dated May 17, 2023.
Office Action issued in corresponding Japanese Patent Application No. 2020-540655, dated Jun. 6, 2023.
Office Action issued in corresponding Korean Patent Application No. 10-2020-7009468 dated Apr. 4, 2024 (13 pages).

* cited by examiner

SOLID W/O COSMETIC COMPOSITION

RELATED APPLICATION

This application claims the priority of U.S. Provisional Application No. 62/627,454 filed on Feb. 7, 2018, which is incorporated herein by reference.

TECHNICAL FIELD

The present invention relates to a solid W/O cosmetic composition(s) and in particular, the improvement of composition(s) containing water and a gellifying system.

BACKGROUND ART

Many of currently available solid cosmetics (skin products and color cosmetics) have been designed to improve physical cosmetic properties (e.g., hardness, texture), as well as the consumer's overall experience related to the use of cosmetic products. Typically, in order to create and maintain the solid structure of cosmetics, a high level of solidifying waxes (e.g., above 15% of the total weight of the composition) and powders/fillers (e.g., above 20% of the total weight of the composition) have been used, and commonly those products are water free. Unfortunately for consumers, the high level of waxes and/or powders make the finished products very stiff and tacky, and cause a drying effect to the skin, and their application appears to be rigid and uneven, resulting in unaesthetic look.

In order to improve the moisturizing effect, some solid cosmetics contain a high level of water and humectants. They are available in liquid or gel forms (for example, lipgloss, lip gel, lip tattoo, lip lacquer, gel eyeliners, gel creams, etc.). Typically, the water based products contain dyes for color appearance and a long lasting effect, which unfortunately for consumers, results in the long term staining of their skin. The stains are hard to remove and can be irritating and drying to the skin. There are also known water bases sticks; however, they contain small amounts of water and no pigments or high amounts of water but they are unstable (e.g., break over time, sweat/perspire water at higher temperature, develop unpleasant odor).

There remains a need for improved solid cosmetic compositions which provide a long term moisturizing and cooling effect, while at the same time are soft, retain stable architecture (do not break or sweat at high temperature and water does not evaporate) over time and maintain a smooth, creamy, air like texture.

CITATION LIST

Patent Literature

PTL 1: U.S. Pat. No. 5,928,655
PTL 2: U.S. Pat. No. 5,756,082
PTL 3: EP Publication No. 1,112,325
PTL 4: U.S. Pat. No. 6,528,073
PTL 5: U.S. Pat. No. 6,280,750
PTL 6: U.S. Pat. No. 5,567,426
PTL 7: U.S. Pat. No. 9,023,334
PTL 8: U.S. Pat. No. 8,597,621

SUMMARY OF INVENTION

The present invention relates to a stable, solid water-in-oil (W/O) emulsion composition(s) comprising at least one gellifying system and at least one surfactant system.

In one embodiment, the gellifying system of the present invention may comprise the combination of at least one (1) hydrophobic gelling agent and at least one (1) hydrophilic gelling agent.

In a further embodiment, the gellifying system comprises at least two (2) hydrophobic gelling agents and at least one (1) hydrophilic gelling agent.

In another embodiment, the at least two hydrophobic gelling agents comprise, for example, styrene-based copolymers and mineral gellants, while the hydrophilic gelling agent comprises, for example, at least one thermoreversible polysaccharide.

The unique combination of the at least two (2) hyrdrophobic gelling agents (e.g., comprising the hydrocarbon styrene copolymers and the hydrophobic mineral gellant(s)) allows for obtaining a solid and smooth texture of the composition. At the same time, the water entrapped within hydrophilic gellant provides a long lasting moisturizing effect, as well as an instant cooling and bursting sensation upon application. The combination of all the gellants contributes to obtaining a long lasting color effect and comfortable wear.

In order to overcome stability issues, in one embodiment of the invention, the composition contains at least one surfactant system comprising at least one nonionic surfactant having HLB value which equals or is less than 14.

Another solution to the stability problems was resolved by introducing at least one surfactant system comprising a blend of at least two nonionic surfactants having HLB value from about 2 to about 14 in addition to at least one polyglycerol ester.

In a particular exemplary embodiment, the at least two nonionic surfactants are selected from, but not limited to, polyethylene glycol dimethicone surfactants.

The unique combination of the nonionic surfactants provides stability of the composition, meaning that the composition remains solid and creamy over time, pigment remains uniformly dispersed, does not break or crack, does not release (sweat) water at higher temperatures, and does not have an unpleasant odor.

One exemplary embodiment of the invention refers to a W/O cosmetic composition, comprising a gellifying system, the gellifying system comprising:
(I) at least one hydrophobic gelling agent comprising a styrene copolymer gelling agent;
(II) at least one hydrophilic gelling agent; and
(III) at least one additional hydrophobic gelling agent comprising a mineral gelling agent, and
at least one emulsifying system comprising at least one polyethylene glycol dimethicone surfactant having HLB value that equals or is less than 14.

Another exemplary embodiment of the invention refers to a solid W/O cosmetic composition comprising:
A. from about 9% to about 50% of an aqueous phase based on the percent weight of the total weight of the composition, comprising at least one hydrophilic gelling agent at the amount from about 0.1% to about 5% by percent weight relative to the percent weight of the aqueous phase;
B. from about 91% to about 50% of an oil phase based on the percent weight of the total weight of the composition, comprising at least one hydrophobic gelling agent at the amount from about 10% to about 30% by percent weight relative to the percent weight of the oil phase; and
at least one surfactant.

In further exemplary embodiments of the invention, the composition further comprises, but is not limited to, one or more of water, at least one wax, at least one fatty solvent, at least one humectant, and at least one texturizing powder. Additionally and optionally, the composition may further comprise at least one film former and/or at least one pigment.

Due to the unique structure described herein below, the inventive compositions are characterized by smooth, creamy and non-tacky texture, while at the same time they provide long lasting, refreshing and cooling sensation and are stable.

The inventive composition can be, but is not limited to, lipsticks, foundations, blushes, eyeshadows, mascaras, eyeliners, skin care products, sun care products, deodorants, etc.

Other exemplary embodiments of the present invention refer to methods of enhancing the appearance of keratinous materials (for example lips, skin, eyelids, eyebrows, etc.,) by applying the inventive composition to such keratinous materials using a suitable applicator, including but not limited to a lipstick case or holder, a mascara applicator, an eye shadow applicator, an eyeliner applicator, a blush applicator, a foundation applicator, by way of example and not limitation.

The solid form of the inventive composition might be but is not limited to a stick, crayon, pod, cane, etc.

Still further exemplary embodiments of the present invention refer to a method of making a solid W/O composition comprising:
(a) preparing at least one oil phase comprising at least one hydrophobic gel;
(b) preparing at least one water phase comprising at least one hydrophilic gel; and
(c) optionally incorporating at least one pigment.

It is to be understood that both the forgoing general description and the following detailed description are exemplary and explanatory only, and are not restrictive of the invention.

DETAILED DESCRIPTION

Percentages are by mass (weight) of the composition or the particular phase being described, unless otherwise specified. All ratios are mass ratios, unless specifically stated otherwise.

"About" as used herein means within 10% of the indicated number (e.g., "about 10%" means 9%-11% and "about 2%" means 1.8%-2.2%)

A "solid cosmetic" means that a composition is characterized by but not limited to hardness from about 7 mm to about 24 mm, preferably from about 10 mm to about 20 mm, most preferably from 12 mm to 16 mm, as measured by ASTM method number 213 (Sun-Rheo Meter, Needle: 1.0 mm; weight 2 kG; hold 10.0 M; Press 20 MM/M) at ambient temperature (25° C.).

A "keratinous surface" as used herein means skin (including face), hair, including eyelashes and eyebrows, that might be treated with skin and/or makeup products (e.g., color cosmetics).

The term "oil phase" as used herein means a phase containing a hydrophobic carrier, typically oily ingredients. Suitable oils include, by way of example and not limitation, silicones oils (linear and cyclic), esters, ketons, glycol ethers vegetable and mineral oils, synthetic oils, paraffinic oils, hydrocarbons, aromatic solvents, including but not limited to those identified herein. The oils may be volatile or non-volatile, and are preferably in the form of pourable liquids at the room temperature (25° C.).

"Volatile" means that the oil has a measurable vapor pressure of at least about 2 mm of mercury at 20° C.

The term "non-volatile" means that the oil has a vapor pressure of less than 2 mm of mercury at 20° C.

The oil phase may contain additional hydrophobic compounds that are easy to incorporate into the hydrophobic carriers. Such other applicable hydrophobic compounds can be in a liquid, solid and/or semi-solid form and they might, for example, include and are not limited to oil dissolvable waxes and film-formers, surfactants, emulsifiers, preservatives, thickeners (gellants), emollients, actives, vitamins, pigments, extracts, powders, hydrophobic solvents, and other useful ingredients.

The term "hydrophobic" typically means that the substance, because of its nonpolar structure, is difficult to dissolve in water. The term "hydrophilic" on another hand means that the substance is dissolvable in water or other polar solvents due to its hydrogen bonding ability.

Some compounds may be characterized by having both hydrophobic and hydrophilic properties.

The term "water phase" is understood to be a phase containing water as the dominant carrier. Typically, the water phase may contain additional substances, for example water dissolvable film-formers, surfactants, emulsifiers, thickeners (gellants), emollients, humectants, preservatives, actives, vitamins, extracts, powders, hydrophilic solvents, and other useful ingredients. Those compounds might be introduced to the composition in the liquid, solid and/or semi-solid form.

In a non-limiting exemplary embodiment, the amount of the oil phase characterizing the inventive composition ranges from about 50% to about 91%, more preferably from about 35% to about 88%, and most preferably from about 50% to about 83% by mass relative to the total mass of the composition.

In a non-limiting exemplary embodiment, the amount of water phase characterizing the inventive composition ranges from about 9% to about 50%, more preferably from about 10% to about 40%, and most preferably from about 12% to about 30% by mass relative to the total mass of the composition.

The compositions and methods of the present invention can comprise, consist of or consist essentially of the essential elements and limitations of the invention described herein, as well as any additional or optional ingredients, components or limitations described herein or otherwise useful.

Gellifying System

The gellifying system of the present invention comprises the combination of at least one hydrophobic gelling agent(s) and at least one hydrophilic gelling agent(s). Preferably, the gellifying system comprises a combination of at least two (2) hydrophobic gelling agents and at least one (1) hydrophilic gelling agent.

As used herein, "gelling agent" means an agent, contributing to modification of viscosity, thixotropic properties and stability of cosmetic compositions (e.g., reduces pigment sedimentation, syneresis).

According to exemplary embodiments of the present invention, the gellifying system ranges from about 3.01% to about 27%, preferably from about 4% to about 21%, and most preferably from about 4% to about 17% by weight relative to the total weight of the composition.

In a specific exemplary embodiment, the weight ratio of the hydrophobic gelling agent(s) and the hydrophilic gelling agent is from about 1.5:0.005 to about 12.5:1.

Further, in the present invention, when using two or more types of hydrophobic gelling agents, at least one is preferably a hydrophobic styrene copolymer gelling agent.

The weight ratio of the hydrophobic styrene copolymer gelling agent and other hydrophobic gelling agent (e.g., hydrophobic mineral gelling agent) is preferably from about 1:0.5 to about 7.5:5.

In a specific exemplary embodiment, the weight ratio of the hydrophobic styrene copolymer gelling agent (i.e., styrene copolymer in carrier) to the hydrophilic gelling agent (i.e., powder only) to the hydrophobic mineral gelling agent (i.e., mineral gallant in carrier) is from about 1:0.005:0.5 to about 7.5:1:5, respectively.

A. Hydrophobic Gelling Agents (Gellants)

As per present invention the cosmetic compositions may include at least one hydrophobic gelling agent (gellants), which include synthetic and/or natural viscosity increasing agents.

Accordingly, as per invention, the composition may contain at least one thickening hydrophobic gelling agent, preferably more than one hydrophobic gelling agent, such as for example hydrocarbon block copolymers, including styrene block copolymers, and hydrophobic minerals and their mixtures thereof.

The hydrophobic gelling agents are typically incorporated into the oil (hydrophobic) phase, containing oils suitable for the use in the compositions of the invention. As per embodiments, the suitable hydrophobic gellants can be used in a form of solids or gels.

In accordance with embodiments of the present invention, the hydrophobic gelling agents are at the amount from about 3% to about 25%, preferably from about 3.5% to about 20% and more preferably from about 6% to about 16% by weight relative to the total weight of the composition.

The presence of the hydrophobic gellant results in a desirable texture as previously described, hardness as well as stability of the finished product.

1. Hydrocarbon-Styrene Copolymer Gellants

In accordance with one embodiment of the present invention, the at least one hydrocarbon block copolymer comprises at least one styrene block and at least one block comprising units chosen from butadiene, ethylene, propylene, butylene and isopropene, and hydrogenated hydrocarbon block copolymers and their mixtures thereof.

Examples of suitable hydrocarbon-based block copolymers are described in U.S. Pat. No. 5,221,534, herein incorporated by reference. The hydrocarbon based block copolymers of the invention are preferably soluble or dispersible in the oil phase.

In one exemplary embodiment of the invention, the hydrocarbon based block copolymer is an amorphous block copolymer of styrene and olefin.

The term "polymers" is intended to mean both copolymers obtained from two types of monomers and those obtained from more than two types of monomers, such as, for example, terpolymers obtained from three types of monomers. The molecules of polymers may contain at least one hydrophilic unit and/or at least one hydrophobic unit.

According to another embodiment, the hydrocarbon block copolymer is a styrene copolymer gelling agent chosen from but not limited to block polymers comprising at least one block composed of styrene units or styrene derivatives.

The copolymer comprising at least one styrene block may be a diblock or triblock copolymer or a multiblock copolymer, star or radial. Particularly useful but not limited examples include ethylene/propylene/styrene copolymer and butylene/ethylene/styrene as per description in U.S. Pat. No. 8,021,674 and for example as described in U.S. Pat. No. 6,433,068, all of which are herein incorporated by reference.

An example of commercially available styrene copolymer gelling agent useful in the invention is Versagel ME 2000 (INCI name: Hydrogenated Polyisobutene (and) Ethylene/Propylene/Styrene Copolymer (and) Butylene/Ethylene/Styrene Copolymer) and other kinds of the gelling agents sold under the VERSAGEL (Registered Trademark) series available from Calumet Penreco. The applicable VERSAGEL (Registered Trademark) gellants contain styrene copolymers in a variety of carriers, such as for example mineral oil, isohexadecane, isododecane, hydrogenated polyisobutane, C12-15 alkyl benzoate, and isonolnyl isononanoate.

In an exemplary embodiment, the amount of the hydrocarbon styrene copolymer gelling agent (i.e., the styrene copolymer in carrier) to be used in the present invention ranges from about 2% to about 15%, more preferably from about 3% to about 12%, and most preferably from about 4% to about 10% by mass relative to the total mass of the composition.

2. Hydrophobic Mineral Gellant(s)

In accordance with the present invention the inventive composition may also contain at least one hydrophobic mineral gellant, which can be chosen from but is not limited to organic modified clays and modified or unmodified hectorites and hydrophobic silicas, including fumed silicas. As per invention, the hydrophobic mineral gelling agents may be selected from, for example, dimethyl distearyl ammonium hectorite, dimethyl distearyl ammonium bentonite, and dimethyl distearyl ammonium modified montmorillonite and others, as described and exemplified in U.S. Pat. Pub. No. 2007/0071703, which is hereby incorporated by reference.

The hydrophobic mineral gelling agents may be those in which a quaternary ammonium salt compound is added to a natural or synthetic smectite clay mineral, such as bentonite, by way of an ion exchange reaction. The choice of organic modified clay minerals is not particularly limited as long as it is cosmetically acceptable and may include, for example, dimethyl ammonium hectorite, benzyl dimethyl stearyl ammonium hectorite, and magnesium aluminum silicate treated with distearyl dimethyl ammonium chloride.

The hydrophobic mineral gellants particularly useful in the invention are selected, for example, from bentonites and organically modified hectorites pre-dispersed in organic solvents. A non-limiting example of commercially available bentonite is BENTONE GEL (Registered Trademark) series, including BENTONE GEL (Registered Trademark) ISD V (INCI: Isododecane, Disteardimonium Hectorite, Propylene Carbonate) available from Elementis Specialties. Another exemplary material is GARAMITE 7308XR (INCI: Quaternium-90 Sepiolite and Quaternium-90 Montmorillonite) available from Eckart.

As already mentioned, another applicable hydrophobic mineral gelling agent comprises silica, in particular fumed silica and those treated with silanol groups. Such hydrophobic silicas are commercially available, for example, under the names of AEROSIL (Registered Trademark) by Degussa and CAB-O-SIL (Registered Trademark) available from Cabot.

As per invention, the suitable mineral gelling agents may be utilized in a solid powder form or a gel, where the powder(s) are dispersed in a carrier, such as for example mineral oil, isohexadecane, isododecane, hydrogenated polyisobutane, C12-15 alkyl benzoate, and/or isonolnyl isononanoate.

In an exemplary embodiment, the amount of the hydrophobic mineral gelling agent (mineral gellant in carrier) ranges from about 1% to about 10%, more preferably from about 1.5% to about 8%, and most preferably from about 2% to about 6% by mass relative to the total mass of the composition.

B. Hydrophilic Gelling Agent

According to the present invention, the composition may include at least one hydrophilic gelling agent. Non-limiting examples of the hydrophilic gelling agent include thermoreversible polysaccharides, e.g., agar, agarose, carrageenan, and gellan. According to embodiments of the invention, the hydrophilic gelling agents can be incorporated into the formulations in the powder form or gels.

In one exemplary embodiment, the at least one hydrophilic gelling agent is an agar as described in U.S. Pat. No. 8,933,134, which is hereby incorporated by reference. An agar useful in exemplary embodiments of the invention is insoluble in cold water, but it swells considerably, absorbing as much as twenty times its own weight of water. It dissolves readily in boiling water and sets to a firm gel at concentrations as low as 0.50%. Another useful example is powdered dry agar that is soluble in water and other solvents at temperatures between 95° C. and 100° C. A still further useful example is moistened agar flocculated by ethanol, 2-propanol or acetone, or salted out by high concentrations of electrolytes, that is soluble in a variety of solvents at room temperature. As per invention, the preferred suitable form of agar is the powder; however, agar can be also introduced to the composition as an agar gel, its preparation and characteristics are disclosed in U.S. Pat. Nos. 9,757,312 and 8,367,044, all of which are hereby incorporated by reference in their entirety. The agar used in connection with embodiments of the invention may be of cosmetic as well as food grade, including the one available from Ina Food Industry Corporation.

The amount of the hydrophilic gelling agent to be used in the present invention ranges but is not limited to from about 0.01% to about 2%, more preferably from about 0.1% to about 1%, and most preferably from about 0.2% to about 0.5% by mass relative to the total mass of the composition.

According to the invention, the presence of the hydrophilic gelling agent allows for optimizing the desired texture and hardness.

As per present invention, the hydrophilic gelling agent might be mixed with water to obtain a hydrophilic gel. The amount of the at least one hydrophilic gel to be used in the present invention ranges but is not limited to from about 9.01% to about 37%, more preferably from about 10.1% to about 31%, and most preferably from about 12.2% to about 25.5% by mass relative to the total mass of the composition.

Surfactant System

As per current invention, the inventive composition contains at least one surfactant system comprising, for example, at least one nonionic surfactant having HLB value which equals or is less than 14.

"HLB" refers to the "hydrophilic-lipophilic balance" associated with emulsifiers.

In particular, HLB value relates to the ratio of hydrophilic groups and lipophilic groups in emulsifiers, and also relates to solubility of the emulsifiers. Typically, lower HLB emulsifiers are more soluble in lipophilic materials or oils and are more appropriate for use in water-in-oil (W/O) emulsions. On the other hand, higher HLB emulsifiers are more soluble in water or hydrophilic materials and are more suitable for oil-in-water (O/W) emulsions.

Additionally, the current invention, may contain for example the surfactant system comprising the blend of at least two nonionic surfactants having HLB value from 2-14. Examples of applicable nonionic surfactants may include polyglycerol alkyl ethers, ester-linked surfactants, polyoxyethylene alkyl ethers, polyglyceryl esters, glyceryl ethers, sorbitan derivatives, including sorbitan esters, polyethylene glycol derivatives of silicones, polyethylene glycol ethers, alkoxylated alcohols, and carbohydrates. By way of further example, the suitable surfactants can include but are not limited to propylene glycol isostearate, glyceryl stearate, sorbitan isostearate, oleth-2, glyceryl laurate, cetheth-2, methyl glucose sesquistearate, laureth-4, ceteryl glucoside, polysorbate 85, oleth-10 and ceteth-10.

Particularly useful in this invention are polyethylene glycol derivatives of dimethicone, specifically PEG-8 to PEG-12 dimethicone surfactants and those described in U.S. Pat. No. 7,842,725. As per one of the embodiments, suitable but nonlimiting examples of polyethylene glycol derivatives of dimethicone are PEG-12 dimethicone and PEG-10 dimethicone, both having HLB value of less than 14.

As per another exemplary embodiment, the inventive composition may contain for example at least two (2) nonionic surfactants.

The amount of the nonionic surfactant to be used in the present invention ranges but is not limited to from about 0.01% to about 4%, more preferably from about 0.1% to about 3%, and most preferably from about 0.2% to about 2.5% by mass relative to the total mass of the composition.

The amount of the PEG-12 dimethicone to be used in the present invention ranges but is not limited to from about 0.01% to about 4%, more preferably from about 0.1% to about 3%, and most preferably from about 0.2% to about 2.5% by mass relative to the total mass of the composition.

The amount of the PEG-10 dimethicone to be used in the present invention ranges but is not limited to from about 0.01% to about 4%, more preferably from about 0.1% to about 3%, and most preferably from about 0.2% to about 2.5% by mass relative to the total mass of the composition.

Further, in an exemplary embodiment, the blend of dimethicone surfactants contains PEG-12 dimethicone and PEG-10 dimethicone at the mass ratio from about 5:1 to about 1:1, based on the total mass of the composition.

Wax

In accordance with some exemplary embodiments of the present invention, at least one wax is included in the composition. The at least one wax is chosen from but not limited to a solid or semisolid waxes at room temperature (25° C.). Specific examples include, but are not limited to, natural and synthetic waxes, for example: beeswax, candelilla wax, cotton wax, carnauba wax, bayberry wax, insect wax (wax secreted by Ericerus pela), spermaceti, montan wax, bran wax (rice wax), capok wax, Japan wax, lanolin acetate, liquid lanolin, sugar cane wax, esters of lanolin fatty acids and isopropyl alcohol, hexyl laurate, reduced lanolin, jojoba wax, hard lanolin, shellac wax, beeswax, microcrystalline wax, paraffin wax, POE lanolin alcohol ethers, POE lanolin alcohol acetates, POE cholesterol ethers, esters of lanolin fatty acids and polyethylene wax, synthetic wax, fatty acid glycerides, hydrogenated castor oil, petrolatum, and POE hydrogenated lanolin alcohol ethers.

The amount of the wax to be used in the present invention ranges but is not limited from about 12% to about 22%, more preferably from about 13% to about 18%, most preferably from about 13% to about 16.5% by mass relative to the total mass of the composition.

Solvents

In accordance with some exemplary embodiments of the present invention, at least one solvent is included in the composition. The at least one solvent is chosen from but not limited to solvents having flash point below 50° C. and those which have flash point above 70° C., that includes volatile and non-volatile hydrocarbons, volatile and nonvolatile silicones, alcohols, glycols, esters, vegetable oils, and synthetic oils. Some preferred solvents include for example hydrocarbon and silicone based solvent, such as hydrogenated polyisobutane, isododecane, dimethicone, and semethicone. A commercially available suitable hydrocarbon solvent is PARLEM 4 (INCI name: Hydrogenated polyisobutane and tocopherol) available from NOF Corporation.

The amount of the solvent to be used in the present invention ranges but is not limited from about 0.01% to about 30%, more preferably from about 0.1% to about 25%, most preferably from about 1% to about 20% by mass relative to the total mass of the composition.

Water

According to preferred embodiments of the invention, the W/O emulsion requires the use of water. As per one exemplary embodiments, the water used in the inventive composition is present from about 9% to about 35%, preferably from about 10% to about 30%, and most preferably from about 12% to about 25%, by mass relative to the total mass of the composition.

Texturizing Powders

In accordance with exemplary embodiments of the present invention, at least one texturing powder is included in the composition. The at least one texturizing powder is chosen from but not limited to mineral and organic fillers of any shape. As per this invention, the texturizing powders can be but are not limited to a blend of silica, polymer microsphere and amino acid. Examples include but are not limited to mica, silica, polyamide powders, starch, boron nitre, silicone resins microbeads, and elastomeric powders.

The amount of the texturizing powers to be used in the present invention ranges but is not limited from about 0.01% to about 30%, more preferably from about 0.1% to about 25%, and most preferably from about 1% to about 20% by mass relative to the total mass of the composition.

Humectants

According to exemplary embodiments of the present invention, the inventive composition contains humectants selected from but not limited to hydrophilic humectants including polyol type humectants such as dipropylene glycol, polyglycerine, 1,3-butylene glycol, ethers, polyols, glycerine, glycerine polymers and polyethylene glycol, as described in U.S. Pat. No. 5,977,188. It was observed, that particularly suitable but not limited humectants that may be used in connection with embodiments of the invention are glycerin and glycerin polymers having up to 40 glycerin units.

The amount of the humectants to be used in the present invention ranges but is not limited from about 0.01% to about 10%, more preferably from about 0.1% to about 5%, and most preferably from about 0.2% to about 2% by mass relative to the total mass of the composition.

Pigments (Optional)

In accordance with the present invention, at least one pigment is chosen from but not limited to organic and inorganic treated pigments, and pigments providing special visual effects, for example. The particular examples include but are not limited to iron oxide, red 7 lake, gonioichromatic pigments.

The amount of the pigments to be used in the present invention ranges but is not limited from about 0.01% to about 30%, more preferably from about 0.1% to about 25%, and most preferably from about 1% to about 20% by mass relative to the total mass of the composition.

Film Formers (Optional)

In accordance with the present invention, at least one film former is chosen from but not limited to water soluble film formers and oil soluble firm formers, acrylic based film formers, silicone based film formers, for example the one described in US2009/001708.

"Film former" or "film forming polymer" as used herein means a polymer or resin that leaves a film on the substrate to which it is applied, for example, after a solvent accompanying the film former has evaporated, absorbed into an/or dissipated on the substrate.

The amount of the film formers to be used in the present invention ranges but is not limited from about 0.01% to about 30%, more preferably from about 0.1% to about 25%, most preferably from about 1% to about 20% by mass relative to the total mass of the composition.

The inventive composition may further include other components appropriate for its intended use such as emollients, organic pigments, preservatives, fillers, actives, sunscreens, additives, additional solvent.

DESCRIPTION OF EMBODIMENTS

Preferable embodiments of the present invention are shown herein below.

TABLE 1

| Phase | | Trade Name | INCI name | Example 1 % weight | Example 2 % weight | Example 3 % weight |
|---|---|---|---|---|---|---|
| | | A-oil phase | Oil Phase | | | |
| Oil phase | A | PARLEAM 4 | HYDROGENATED POLYISOBUTENE, TOCOPHEROL | 17.48 | 12.28 | 11.73 |
| Oil phase | A | PERFORMA V825 POLYMER | SYNTHETIC WAX | 4.5 | 4.5 | 4.5 |
| Oil phase | A | VERSAGEL ME 2000* | HYDROGENATED POLYTSOBUTENE, ETHYLENE/PROPYLENE/STYRENE COPOLYMER, BUTYLENE/ ETHYLENE/STYRENE COPOLYMER, BHT | 7 | 7 | 7 |
| Oil phase | B | BENTONE GEL ISD** | ISODODECANE, DISTEARDIMONIUM HECTORITE, PROPYTENE CARBONATE | 3 | 3 | 5 |

TABLE 1-continued

| Phase | | Trade Name | INCI name | Example 1 % weight | Example 2 % weight | Example 3 % weight |
|---|---|---|---|---|---|---|
| Oil phase | C | ACTICIRE | JOJOBA ESTERS, *HELIANTHUS ANNUUS* (SUNFLOWER) SEED WAX, *ACACIA DECURRENS* FLOWER WAX, POLYGLYCERIN-3 | 4 | 4 | 4 |
| Oil phase | C | PERFORMALENE | POLYETHYLENE | 11.75 | 11.75 | 11.75 |
| Oil phase | D | DOW CORNING TORAY SH3773M | PEG-12 DIMETHICONE, TOCOPHEROL | 1 | 1 | 1 |
| Oil phase | D | KF 6051 | PEG-10 DIMETHICONE, TOCOPHEROL | 0.25 | 0.5 | 1 |
| Oil phase | D | VEGELIGHT | C9-12 ALKANE, COCO-CAPRYLATE/CAPRATE | 7 | 7 | 7 |
| Oil phase | D | PERMETHYL 99a | ISODODECANE | 4 | 4 | 2 |
| Oil phase | E | SATINNIER M5 | SILICA | 2 | 2 | 2 |
| Oil phase | E | PLASTIC POWDER D-400 | HDI/TRIMETHYLOL HEXYLLACTONE CROSSPOLYMER, SILICA | 2 | 2 | 2 |
| Oil phase | E | AMIHOPE LL | LAUROYL LYSINE | 3 | 3 | 3 |
| Oil phase | E | CASHMIR B-3 | MICA, SILICA | 2 | 2 | 2 |
| Oil phase | E | TSA 750S | SIMETHICONE | 0.02 | 0.02 | 0.02 |
| B-water phase | | | Water phase | | | |
| water phase | F | DEIONIZED WATER | WATER | 15 | 20 | 20 |
| water phase | F | GLYCERINE | GLYCERIN | 0.25 | 0.25 | 0.25 |
| water phase | F | INA AGAR*** | AGAR | 0.25 | 0.2 | 0.25 |
| water phase | F | PHENOXYETHANOL | PHENOXYETHANOL | 0.5 | 0.5 | 0.5 |
| C-powder phase | | | Pigments phase | | | |
| powder phase | G | SW PIGMENTS GRINDS | SYNTHETIC WAX, TITANIUM DIOXIDE, IRON OXIDES, IRON OXIDES, RED 7 LAKE, IRON OXIDES, ISOPROPYL TITANIUM TRIISOSTEARATE, YELLOW 5 LAKE, RED 6, BLUE 1 LAKE | 15 | 15 | 15 |
| | | | | 100 | 100 | 100 |
| Hardness data done for 28 shades | | | | 7-24 mm | n/a | n/a |

*Versagel ME2000 and
**Bentone- are both incorporated into the exemplified compositions in the form of gels.
***Agar is incorporated into the exemplified compositions in the solid form.

Method of Making the Inventive Composition(s):

In the main beaker, all (A) compounds of the oil phase were combined and homogenized at 90-95° C. until the mixture was uniform. Then, Bentone (B) was added and homogenized at the same temperature for about 5 minutes or until it was completely dispersed within the blend of compounds A. Next, the temperature was lowered to 85-90° C. and all waxes (compounds C) were added and completely melted. After obtaining the homogeneous mixture, all volatile solvents (D) were added and mixed for additional 5 minutes, while maintaining stable temperature of 85-90° C. After that, the temperature was lowered to 80-85° C. and all powders (E) were added and mixed until they were all uniformly dispersed.

In a separate beaker combined compounds of water phase (F). In order to minimize water loss, the water phase was mixed under cover at 80-85° C. After obtaining the uniform mixture, the water phase was slowly added to the oil phase and homogenized using speed of 1700 rpm to 2300 rpm. In order to obtain the uniform composition, the mixture of oil phase and water phase was homogenized for next five (5) minutes at the speed from 1400 rpm to 1700 rpm. The whole procedure of emulsification was done at 80-85° C. All homogenization steps were done by using Romobics homogenizer. After emulsification process was completed, all desired pigments (G) were added and uniformly mixed by using IKA RW mixer.

The inventors carried out tests demonstrating the importance of the use of the described hereinabove gelling system and the surfactant system. The results thereof are shown herein below. The control formulation used in each test represents Example 1 of Table 1.

Evaluation Criteria/Evaluation Methods

The inventive composition was evaluated against comparative examples as presented herein below in Tables 2, 3 and 4 respectively.

Texture

Five (5) independent participants, typical lipstick users, ranging in age from 24-60 applied the lipstick compositions and evaluated them for the following characteristics: light weight, hydration, refreshing and cooling sensation, soft, smooth, creamy, good and comfortable coverage. In addition, the durability of wear was assessed after four (4) hours after application. All parameters were rated using the grading scale from 1 to 3, as described below:
  3: Very good: Panelists reported lipsticks having all characteristics as listed hereinabove.
  2: Acceptable: Panelists reported lipsticks having only some of the characteristics listed hereinabove.
  1: Not acceptable: Panelists reported lipsticks having none of the characteristics listed hereinabove.

Hardness

The hardness was evaluated as per method described hereinabove for each of the tested compositions, using three (3) samples per each of the formulas and an average was calculated. Its acceptance was rated based on the measured values as listed below.
  ○: Good: Hardness ideally from 12 mm-16 mm
  Δ: Acceptable: Hardness 10-20 mm
  x: Not acceptable: Hardness is less than 9 mm or greater than 24 mm Emulsion Separation The emulsion separation of the tested samples was visually inspected immediately after the compositions were made according to the scale below.

○: Good: No separation
x: Not acceptable: Separation.

Stability

The stability of the tested samples was visually evaluated for odor, break and/or "sweating" of solvents. The samples were stored at 0° C., −5° C., 25° C., 37° C. and 98% humidity, and at 45° C. The assessment was made at the time the samples were made (initial) and every week for the total of eight (8) weeks. The acceptance was determined based on presence of odor, break and/or "sweating" of solvents, according to the grading system below:
  ○: Good: No break, odor or sweat at any of the test temperatures during the experimentation time.
  x: Not acceptable: Presence of break/sweat/odor at any temperature listed.

First of all, the inventors studied the need of the use of the combination of three (3) gellants: hydrocarbon styrene copolymer gelling agent (Versagel), hydrophobic mineral gelling agent (Bentone) and hydrophilic gelling agent (Agar).

The compositions used for Examples 2-1 through 2-7 are set forth in Table 2-1. The results are shown in Table 2-2.

TABLE 2-1

| INCI | Exp. 1 | Comp. 2-5 | Comp. 2-6 | Comp. 2-7 | Comp. 2-2 | Comp. 2-4 | Comp. 2-3 |
|---|---|---|---|---|---|---|---|
| HYDROGENATED POLYISOBUTENE & TOCOPHEROL | 17.55 | 20.55 | 27.55 | 24.55 | 20.30 | 27.55 | 17.55 |
| WATER | 15.00 | 15.25 | 15.00 | 15.25 | 15.25 | 15.00 | 15.25 |
| SYNTHETIC WAX & RED 7 LAKE & YELLOW 6 LAKE & RED 6 & IRON OXIDES & YELLOW 5 LAKE & ISOPROPYL TITANIUM TRIISOSTEARATE & TITANIUM DIOXIDE & IRON OXIDES & IRON OXIDES & BLUE 1 LAKE | 14.10 | 14.10 | 14.10 | 14.10 | 14.10 | 14.10 | 14.10 |
| POLYETHYLENE | 7.20 | 7.20 | 7.20 | 7.20 | 7.20 | 7.20 | 7.20 |
| HYDROGENATED POLYISOBUTENE & ETHYLENE/PROPYLENE/STYRENE COPOLYMER & BUTYLENE/ETHYLENE/STYRENE COPOLYMER & BHT* | 7.00 | 7.00 | 0.00 | 0.00 | 7.00 | 7.00 | 7.00 |
| C9-12 ALKANE & COCO-CAPRYLATE/CAPRATE | 6.79 | 6.79 | 6.79 | 6.79 | 6.79 | 6.79 | 6.79 |
| SYNTHETIC WAX | 5.65 | 5.65 | 5.65 | 5.65 | 5.65 | 5.65 | 5.65 |
| POLYETHYLENE | 4.56 | 4.56 | 4.56 | 4.56 | 4.56 | 4.56 | 4.56 |
| ISODODECANE | 4.00 | 4.00 | 4.00 | 4.00 | 4.00 | 4.00 | 4.00 |
| JOJOBA ESTERS & *HELIANTHUS ANNUUS* (SUNFLOWER) SEED WAX & *ACACIA DECURRENS* FLOWER WAX & POLYGLYCERIN-3 | 4.00 | 4.00 | 4.00 | 4.00 | 4.00 | 4.00 | 4.00 |
| LAUROYL LYSINE | 3.00 | 3.00 | 3.00 | 3.00 | 3.00 | 3.00 | 3.00 |
| ISODODECANE & DISTEARDIMONIUM HECTORITE & PROPYLENE CARBONATE** | 3.00 | 0.00 | 0.00 | 3.00 | 0.00 | 0.00 | 3.00 |
| SILICA | 2.00 | 2.00 | 2.00 | 2.00 | 2.00 | 2.00 | 2.00 |
| HDI/TRIMETHYLOL HEXYLLACTONE CROSSPOLYMER & SILICA | 2.00 | 2.00 | 2.00 | 2.00 | 2.00 | 2.00 | 2.00 |
| MICA & SILICA | 1.88 | 1.88 | 1.88 | 1.88 | 1.88 | 1.88 | 1.88 |
| PEG-12 DIMETHICONE & TOCOPHEROL | 1.00 | 1.00 | 1.00 | 1.00 | 1.00 | 1.00 | 1.00 |
| PHENOXYETHANOL | 0.50 | 0.50 | 0.50 | 0.50 | 0.50 | 0.50 | 0.50 |
| PEG-10 DIMETHICONE & TOCOPHEROL | 0.25 | 0.25 | 0.25 | 0.25 | 0.25 | 0.25 | 0.25 |
| AGAR*** | 0.25 | 0.00 | 0.25 | 0.00 | 0.25 | 0.25 | 0.00 |
| GLYCERIN | 0.25 | 0.25 | 0.25 | 0.25 | 0.25 | 0.25 | 0.25 |
| SIMETHICONE | 0.02 | 0.02 | 0.02 | 0.02 | 0.02 | 0.02 | 0.02 |

*Versagel ME2000 and
**Bentone- are both incorporated into the exemplified compositions in the form of gels.
***Agar is incorporated into the exemplified compositions in the solid form.

TABLE 2-2

| ASSESSED CHARACTERISTIC | Exp. 1 | Comp. 2-5 | Comp. 2-6 | Comp. 2-7 | Comp. 2-2 | Comp. 2-4 | Comp. 2-3 |
|---|---|---|---|---|---|---|---|
| Texture | 3 | 2 | 2 | 1 | 2 | 2 | 2 |
| Hardness | ○ | X | X | Δ | Δ | Δ | Δ |
| Emulsion Separation | ○ | X | X | X | X | X | X |
| Stability | ○ | X | X | X | X | X | X |

*Versagel ME2000 and Bentone
**- are both incorporated into the exemplified compositions in the form of gels.
***Agar is incorporated into the exemplified compositions in the solid form.

Example Exp. 1 in Tables 2-1 and 2.2 represents a composition similar to composition 1 from Table 1. Examples from 2-2 to 2-7 are comparative compositions.

As it is shown in Tables 2-1 and 2.2, even if the wax is blended at an amount sufficient for general solidification of the oil phase, appropriate solidification is difficult for the composition that comprises water and the surfactant. In the systems (2-2 to 2-7) incorporating single gellants or blending only of two of them, solidification is insufficient, and they are not preferable in view of stability, hardness, emulsion separation and texture.

The data presented in Tables 2-1 and 2-2 clearly indicates that in order to obtain a stable composition, having the desired hardness and texture, the use of three (3) gellants is necessary.

Next, the inventors investigated the preferred quantities for each of three (3) gellants: hydrocarbon styrene copolymer gelling agent, hydrophobic mineral gelling agent and hydrophilic gelling agent. The results are shown in Tables 3-1 and 3-2.

TABLE 3-1

| INCI | Exp. 1 | Comp. 3-1 | Comp. 3-2 | Comp. 3-4 | Comp. 3-3 |
|---|---|---|---|---|---|
| HYDROGENATED POLYISOBUTENE & TOCOPHEROL | 17.550 | 17.550 | 14.070 | 13.160 | 17.550 |
| WATER | 15.000 | 15.000 | 13.050 | 40.000 | 15.000 |
| SYNTHETIC WAX & RED 7 LAKE & YELLOW 6 LAKE & RED 6 & IRON OXIDES & YELLOW 5 LAKE & ISOPROPYL TITANIUM TRIISOSTEARATE & TITANIUM DIOXIDE & IRON OXIDES & IRON OXIDES & BLUE 1 LAKE | 14.100 | 14.100 | 12.180 | 10.580 | |
| POLYETHYLENE | 7.200 | 7.200 | 6.260 | 5.400 | 7.200 |
| HYDROGENATED POLYISOBUTENE & ETHYLENE/PROPYLENE/STYRENE COPOLYMER & BUTYLENE/ETHYLENE/STYRENE COPOLYMER & BHT* | 7.000 | 20.000 | 20.000 | 5.250 | 7.000 |
| C9-12 ALKANE & COCO-CAPRYLATE/CAPRATE | 6.790 | 6.790 | 5.900 | 5.090 | 6.790 |
| SYNTHETIC WAX | 5.650 | 5.650 | 4.911 | 0.470 | 4.298 |
| POLYETHYLENE | 4.560 | 4.560 | 3.960 | 3.420 | 4.560 |
| ISODODECANE | 4.000 | 4.000 | 3.480 | 3.000 | 4.000 |
| JOJOBA ESTERS & *HELIANTHUS ANNUUS* (SUNFLOWER) SEED WAX & *ACACIA DECURRENS* FLOWER WAX & POLYGLYCERIN-3 | 4.000 | 4.000 | 3.480 | 3.000 | 4.000 |
| LAUROYL LYSINE | 3.000 | 3.000 | 2.610 | 2.250 | 3.000 |
| ISODODECANE & DISTEARDIMONIUM HECTORITE & PROPYLENE CARBONATE** | 3.000 | 3.000 | 3.000 | 2.250 | 15.000 |
| HDI/TRIMETHYLOL HEXYLLACTONE CROSSPOLYMER & SILICA | 2.000 | 2.000 | 1.740 | 1.500 | 2.000 |
| SILICA | 2.000 | 2.000 | 1.740 | 1.500 | 2.000 |
| MICA & SILICA | 1.880 | 1.880 | 1.630 | 1.410 | 1.880 |
| PEG-12 DIMETHICONE & TOCOPHEROL | 1.000 | 1.000 | 0.870 | 0.750 | 1.000 |
| PHENOXYETHANOL | 0.500 | 0.500 | 0.430 | 0.380 | 0.500 |
| PEG-10 DIMETHICONE & TOCOPHEROL | 0.250 | 0.250 | 0.210 | 0.190 | 0.250 |
| AGAR*** | 0.250 | 0.250 | 0.250 | 0.190 | 0.250 |
| GLYCERIN | 0.250 | 0.250 | 0.210 | 0.190 | 0.250 |
| SIMETHICONE | 0.020 | 0.020 | 0.020 | 0.020 | 0.020 |
| SYNTHETIC WAX & IRON OXIDES & IRON OXIDES & IRON OXIDES & RED 7 LAKE & ISOPROPYL TITANIUM TRIISOSTEARATE & TITANIUM DIOXIDE & RED 6 & BLUE 1 LAKE | | | | | 15.452000 |

*Versagel ME2000 and Bentone**—are both incorporated into the exemplified compositions in the form of gels.
***Agar is incorporated into the exemplified compositions in the solid form.

TABLE 3-2

| ASSESSED CHARACTER-ISTIC | Exp. 1 | Comp. 3-1 | Comp. 3-2 | Comp. 3-4 | Comp. 3-3 |
|---|---|---|---|---|---|
| Texture | 3 | 2 | 2 | 2 | 2 |
| Hardness | ○ | Δ | Δ | X | X |
| Emulsion Separation | ○ | X | X | Δ | X |
| Stability | ○ | X | X | X | X |

Example Exp. 1 in Tables 3-1 and 3-2 is the same as Exp. 1 in Tables 2-1 and 2-2 and represents a composition similar to composition 1 from Table 1. Examples from 3-1 to 3-4 are comparative compositions.

As shown in Tables 3-1 and 3-2, hardness, texture, emulsion separation and stability tend to be deteriorated when the styrene copolymer gelling agent is used above 15% of the total weight of the composition (3-1). Similarly, it was observed that all the desired characteristic of the finished inventive composition worsened when hydrophilic gelling agent was used at amounts greater than 3% percent based on the total weight of the composition, as well as when the hydrophobic mineral gelling agent was used above 15%.

The presented data indicates the necessity of the use of the combination of three (3) gellants at specific amounts, which is necessary to obtain the desired properties of the inventive compositions.

Next, the inventors studied the importance of amounts of the specific surfactants, as well as their pH values. The results are shown in Tables 4-1 and 4-2.

TABLE 4-1

| INCI | Exp. 1 | Comp. 4-7 | Comp. 4-6 | Comp. 4-5 | Comp. 4-1 | Comp. 4-2 | Comp. 4-3 |
|---|---|---|---|---|---|---|---|
| HYDROGENATED POLYISOBUTENE & TOCOPHEROL | 17.55 | 17.55 | 12.55 | 11.80 | 18.55 | 17.80 | 18.80 |
| WATER | 15.00 | 15.00 | 15.00 | 15.00 | 15.00 | 15.00 | 15.00 |
| TITANIUM DIOXIDE & SYNTHETIC WAX & IRON OXIDES & RED 7 LAKE & IRON OXIDES & ISOPROPYL TITANIUM TRIISOSTEARATE & YELLOW 5 LAKE & IRON OXIDES & RED 6 & BLUE 1 LAKE & YELLOW 6 LAKE | 13.78 | | | | | | |
| POLYETHYLENE | 7.20 | 7.20 | 7.20 | 7.20 | 7.20 | 7.20 | 7.20 |
| HYDROGENATED POLYISOBUTENE & ETHYLENE/PROPYLENE/STYRENE COPOLYMER & BUTYLENE/ETHYLENE/STYRENE COPOLYMER & BHT* | 7.00 | 7.00 | 7.00 | 7.00 | 7.00 | 7.00 | 7.00 |
| C9-12 ALKANE & COCO-CAPRYLATE/CAPRATE | 6.79 | 6.79 | 6.79 | 6.79 | 6.79 | 6.79 | 6.79 |
| SYNTHETIC WAX | 5.97 | 5.65 | 4.30 | 4.30 | 4.30 | 4.30 | 4.30 |
| POLYETHYLENE | 4.56 | 4.56 | 4.56 | 4.56 | 4.56 | 4.56 | 4.56 |
| ISODODECANE | 4.00 | 4.00 | 4.00 | 4.00 | 4.00 | 4.00 | 4.00 |
| JOJOBA ESTERS & *HELIANTHUS ANNUUS* (SUNFLOWER) SEED WAX & *ACACIA DECURRENS* FLOWER WAX & POLYGLYCERIN-3 | 4.00 | 4.00 | 4.00 | 4.00 | 4.00 | 4.00 | 4.00 |
| LAUROYL LYSINE | 3.00 | 3.00 | 3.00 | 3.00 | 3.00 | 3.00 | 3.00 |
| ISODODECANE & DISTEARDIMONIUM HECTORITE & PROPYLENE CARBONATE** | 3.00 | 3.00 | 3.00 | 3.00 | 3.00 | 3.00 | 3.00 |
| HDI/TRIMETHYLOL HEXYLLACTONE CROSSPOLYMER & SILICA | 2.00 | 2.00 | 2.00 | 2.00 | 2.00 | 2.00 | 2.00 |
| SILICA | 2.00 | 2.00 | 2.00 | 2.00 | 2.00 | 2.00 | 2.00 |
| MICA & SILICA | 1.88 | 1.88 | 1.88 | 1.88 | 1.88 | 1.88 | 1.88 |
| PEG-100 HYDROGENATED CASTOR OIL & TOCOPHEROL | 1.25 | | | | | | |
| PHENOXYETHANOL | 0.50 | 0.50 | 0.50 | 0.50 | 0.50 | 0.50 | 0.50 |
| AGAR*** | 0.25 | 0.25 | 0.25 | 0.25 | 0.25 | 0.25 | 0.25 |
| GLYCERIN | 0.25 | 0.25 | 0.25 | 0.25 | 0.25 | 0.25 | 0.25 |
| SIMETHICONE | 0.02 | 0.02 | 0.02 | 0.02 | 0.02 | 0.02 | 0.02 |
| PEG-10 DIMETHICONE & TOCOPHEROL | 0.00 | 0.25 | 0.25 | 6.00 | 0.25 | 0.00 | 0.00 |
| SYNTHETIC WAX & IRON OXIDES & IRON OXIDES & IRON OXIDES & RED 7 LAKE & ISOPROPYL TITANIUM TRIISOSTEARATE & TITANIUM DIOXIDE & RED 6 & BLUE 1 LAKE | | | 15.45 | 15.45 | 15.45 | 15.45 | 15.45 |
| SYNTHETIC WAX & RED 7 LAKE & YELLOW 6 LAKE & RED 6 & IRON OXIDES & YELLOW 5 LAKE & ISOPROPYL TITANIUM TRIISOSTEARATE & TITANIUM DIOXIDE & IRON OXIDES & IRON OXIDES & BLUE 1 LAKE | | 14.10 | | | | | |
| PEG-12 DIMETHICONE & TOCOPHEROL | | 1.00 | 6.00 | 1.00 | 0.00 | 1.00 | 0.00 |

*Versagel ME2000 and Bentone
**are both incorporated into the exemplified compositions in the form of gels.
***Agar is incorporated into the exemplified compositions in the solid form.

TABLE 4-2

| ASSESSED CHARACTERISTIC | Exp. 1 | Comp. 4-7 | Comp. 4-6 | Comp. 4-5 | Comp. 4-1 | Comp. 4-2 | Comp. 4-3 |
|---|---|---|---|---|---|---|---|
| Texture | 3 | 2 | 1 | 1 | 1 | 1 | 1 |
| Hardness | ○ | Δ | X | X | X | Δ | X |
| Emulsion Separation | ○ | ○ | X | X | X | Δ | X |
| Stability | ○ | ○ | X | X | X | X | X |

Example Exp. 1 in Tables 4-1 and 4-2 is the same as Exp. 1 in Tables 2-1, 2-2, 3-1 and 3-2 and represents a composition similar to composition 1 from Table 1. Examples from 4-1 to 4-7 are comparative compositions.

As demonstrated in Tables 4-1 and 4-2, the presence of polyethylene glycol dimethicone surfactants is preferable in terms of the desired product physical characteristics. It was observed that both the absence and/or too high amount of any of the tested surfactants negatively effected not only the texture but also dramatically deteriorated the composition's hardness, emulsion separation and stability. As per the experiments, to obtain the best quality inventive compositions, PEG12-dimethicone and PEG10-dimethicone should be used simultaneously.

Further, it was found that the optimum HLB of the surfactant is from 2 to 14. Texture and hardness specifically got worsened when the surfactant having the HLB of 16.5 was used.

The invention claimed is:

1. A solid W/O composition, comprising:
   1) gelling agents consisting of:
      bentonite; a hydrocarbon styrene copolymer gelling agent; and
      agar; and
   2) an emulsifying system comprising polyethylene glycol 12 derivative of dimethicone and polyethylene glycol 10 derivative of dimethicone,
   the composition comprises an oil phase and an aqueous phase dispersed in the oil phase,
   wherein the aqueous phase comprises water and the agar; and the oil phase comprises the bentonite, the hydrocarbon styrene copolymer gelling agent and at least one solvent selected from the group consisting of volatile and non-volatile hydrocarbons, volatile and non-volatile silicones, alcohols, glycols, esters, vegetable oils, and synthetic oils,
   wherein the amount of the at least one solvent is from 0.1% to 25%, by mass relative to the total mass of the composition and the amount of the water is from 9% to 25%, by mass relative to the total mass of the composition,
   wherein the composition further comprises at least one wax,
   wherein the amount of the least one wax is from 12% to 22% by mass relative to the total mass of the composition,
   wherein the amount of the bentonite is about 3 mass %, the amount of the hydrocarbon styrene copolymer gelling agent is about 7 mass %, the amount of the agar is about 0.025 mass %, the amount of the polyethylene glycol 12 derivative of dimethicone is about 0.25 mass % and the amount of the polyethylene glycol 10 derivative of dimethicone is about 1.00 mass %.

2. The composition according to claim 1, wherein the at least one solvent is selected from the group consisting of hydrogenated polyisobutane, isododecane, dimethicone, and simethicone.

3. The composition according to claim 2, wherein the amount of the at least one solvent by mass relative to the total mass of the composition is from 1% to 20%.

4. The composition according to claim 1, further comprising at least one humectant.

5. The composition according to claim 1, further comprising at least one texturizing powder.

6. The composition according to claim 1, further comprising at least one pigment.

7. A lipstick comprising the composition according to claim 1.

8. A method of enhancing the appearance of keratinous materials comprising applying the composition of claim 1.

9. A solid W/O cosmetic emulsion composition, comprising:
   from 9% to 50% of an aqueous phase based on the percent mass of the total mass of the composition, comprising (i) water and (ii) agar;
   from 50% to 91% of an oil phase based on the percent mass of the total mass of the composition, comprising (i) at least one solvent and (ii) at least two hydrophobic gelling agents; and at least one surfactant,
   wherein the at least two hydrophobic gelling agents are bentonite and a hydrocarbon styrene copolymer gelling agent;
   the at least one surfactant comprises polyethylene glycol 12 derivative of dimethicone and polyethylene glycol 10 derivative of dimethicone;
   gelling agents of the composition consist of the agar, the bentonite and the hydrocarbon styrene copolymer gelling agent;
   the at least one solvent is selected from the group consisting of volatile and non-volatile hydrocarbons, volatile and non-volatile silicones, alcohols, glycols, esters, vegetable oils, and synthetic oils,
   the amount of the at least one solvent is from 0.1% to 25%, by mass relative to the total mass of the composition,
   the amount of the water is from 9% to 25%, by mass relative to the total mass of the composition, wherein the composition further comprises at least one wax and wherein the amount of the least one wax is from 12% to 22% by mass relative to the total mass of the composition,
   wherein the amount of the bentonite is about 3 mass %, the amount of the hydrocarbon styrene copolymer gelling agent is about 7 mass %, the amount of the agar is about 0.025 mass %, the amount of the polyethylene glycol 12 derivative of dimethicone is about 0.25 mass % and the amount of the polyethylene glycol 10 derivative of dimethicone is about 1.00 mass %.

10. The composition according to claim 9, wherein the at least one solvent is selected from the group consisting of hydrogenated polyisobutane, isododecane, dimethicone, and simethicone.

11. The composition according to claim 10, wherein the amount of the at least one solvent by mass relative to the total mass of the composition is from 1% to 20%.

* * * * *